United States Patent [19]

Martindale et al.

[11] Patent Number: 4,795,844

[45] Date of Patent: Jan. 3, 1989

[54] PROCESS FOR CONVERSION OF LIGHT OLEFINS TO LPG AND AROMATICS

[75] Inventors: David C. Martindale, Roselle; Ronald E. Andermann, Arlington Heights; John R. Mowry, Des Plaines, all of Ill.

[73] Assignee: UOP Inc., Des Plaines, Ill.

[21] Appl. No.: 75,383

[22] Filed: Jul. 20, 1987

[51] Int. Cl.$^4$ ............................................. C07C 12/02
[52] U.S. Cl. .................................................... 585/415
[58] Field of Search ........................................ 585/415

[56] References Cited

U.S. PATENT DOCUMENTS

| | | | |
|---|---|---|---|
| 2,972,643 | 2/1961 | Kimberlin | 260/673 |
| 2,992,283 | 7/1961 | Eng | 260/673 |
| 3,761,389 | 9/1973 | Rollmann | 208/64 |
| 4,180,689 | 12/1979 | Davies et al. | 585/407 |
| 4,329,532 | 5/1982 | Conn et al. | 585/407 |
| 4,437,394 | 8/1982 | Detz et al. | 585/419 |
| 4,451,685 | 5/1984 | Nevitt et al. | 585/415 |
| 4,528,412 | 7/1985 | Steacy | 585/415 |
| 4,579,988 | 4/1986 | Kieffer | 585/415 |
| 4,634,799 | 1/1987 | Haun et al. | 585/415 |

FOREIGN PATENT DOCUMENTS 0162636  11/1985  European Pat. Off. .

OTHER PUBLICATIONS

Csicsery, Sigmund M., "Dehydrocyclodimerization," Ind. Eng. Chem. Process Des. Dev., vol. 18, No. 2, 1979, p. 191.

Primary Examiner—Curtis R. Davis
Attorney, Agent, or Firm—Thomas K. McBride; John F. Spears, Jr.

[57] ABSTRACT

A process is disclosed for the catalytic conversion of an olefin-containing $C_3$ and/or $C_4$ feed (1) into aromatic hydrocarbons (22) and $C_3$ and/or $C_4$ paraffins (25,26). The process may result in a net consumption of hydrogen and operates at relatively mild temperature conditions, with preferred temperatures in the reaction zone (4) being less than 425 degrees Celsius. The severity of the operating conditions and the length of time the catalyst is used are controlled to hold down total carbon deposition and to increase aromatics selectivity. A catalyst comprising gallium supported on a zeolite containing base is preferred. The feed stream contains a mixture of paraffins and olefins, with aromatics production being directly related to feed olefin content.

7 Claims, 1 Drawing Sheet

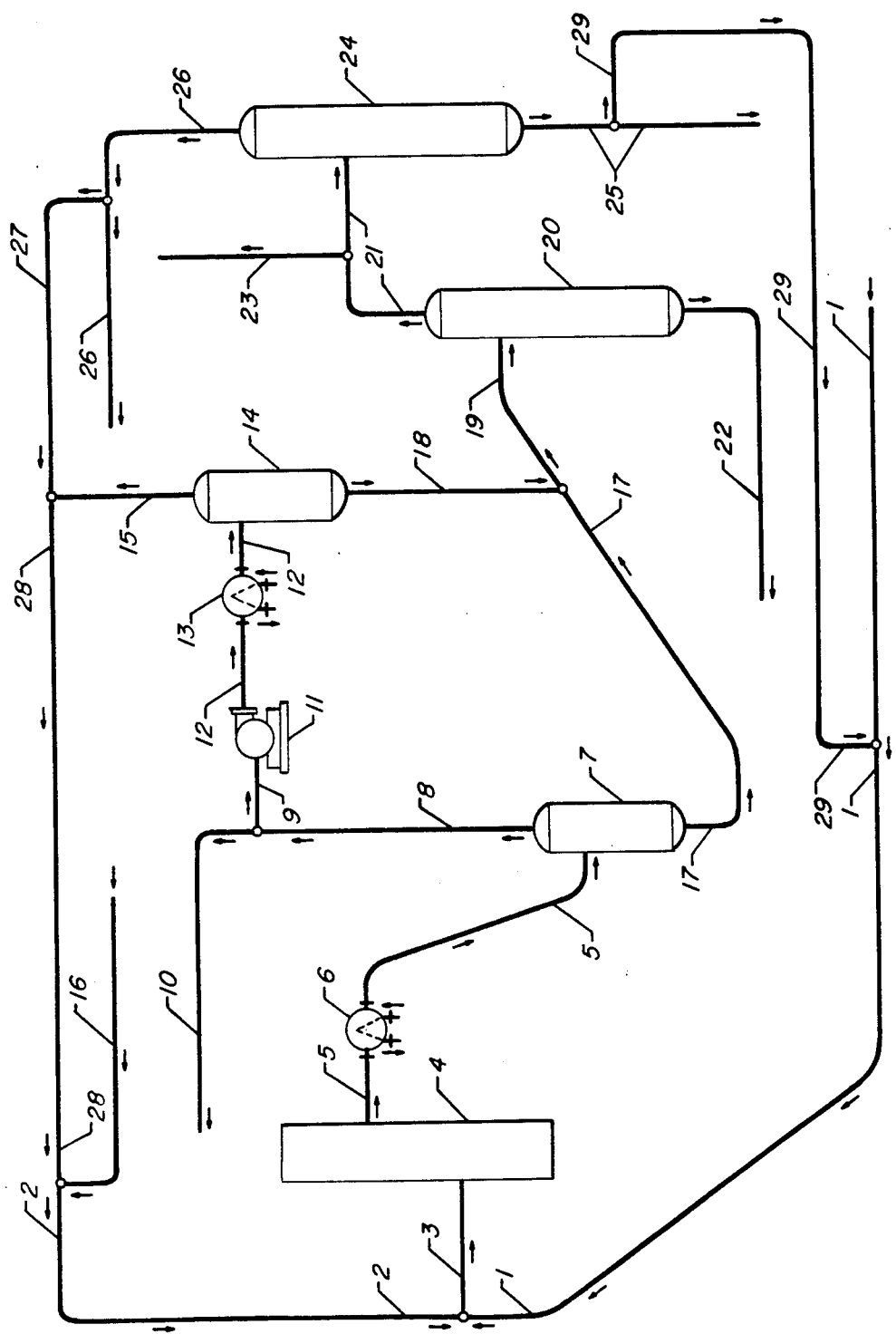

PROCESS FOR CONVERSION OF LIGHT OLEFINS TO LPG AND AROMATICS

FIELD OF THE IVVENTION

The subject process relates to a hydrocarbon conversion process wherein high quality (low olefin content) LPG is produced from a feed stream containing a sizable concentration of light olefinic hydrocarbons. The subject process also relates to a catalytic process referred to as dehydrocyclodimerization (DHCD) wherein two or more molecules of a light aliphatic hydrocarbon, such as propane or propylene, are joined together to form a product aromatic hydrocarbon. A limited embodiment of the invention specifically relates to a low severity DHCD process, characterized by net hydrogen consumption and a low reaction zone operating temperature. The process is effective in converting a mixture of paraffins and olefins into a first product stream consisting essentially of aromatics and a second pooduct stream consisting of paraffins equal in carbon number to the feed olefins. The subject process therefore results in selective conversion of the olefins to aromatic hydrocarbons and paraffins.

INFORMATION DISCLOSURE

There are a large number of references which describe the conversion of light aliphatic hydoocarbons to aromatic hydrocarbons. For instance, U.S. Pat. No. 2,992,283 issued to J. Eng describes the conversion of propylene to a variety of higher molecular weight saturated and unsaturated hydrocarbons including aromatics using a treated crystalline aluminosilicate as the catalyst. This reference indicates a temperature from 300 to 1200 degrees Fahrenheit (149–643 degrees Celsius) can be employed, with 400 to 800 degrees Fahrenheit (204 to 426 degrees Celsius) being a preferred temperature range. U.S. Pat. No. 4,347,394 issued to C. M. Detz et al describes the conversion of $C_5$-plus hydrocarbons to aromatics using a nonacidic zeolite supporting a platinum compound at temperatures above 480 degrees Celsius.

U.S. Pat. No. 4,451,685 issued to T. D. Nevitt et al. presents a process for conversion of ethylene and/or propylene to gasoline blending stocks containing aliphatics and aromatics over crystalline borosilicate catalysts at a temperature of 300 to 500 degrees Celsius. It appears the product of the conversion of pure propylene is predominantly nonaromatics, with a maximum production of 34 weight percent aromatics being reported for a comparison using a ZSM-5 catalyst. U.S. Pat. No. 4,329,532 issued to P. J. Conn et al describes the conversion of $C_4$-minus olefins or mixtures of olefins and paraffins to aromatic hydrocarbons in a temperature range of from 350 to 550 degrees Celsius. The catalyst comprises a crystalline silicate having a specified composition, crystallite size range, and X-ray diffraction pattern.

A review of dehydrocyclodimerization was published at page 191 of Volume 18, No. 2 (1979) of *Industrial and Engineering Chemistry*— "Process Design and Development" by S. M. Csicery. This review states dehydrocyclodimerization is carried at a temperature above 430 degrees Celsius in the absence of added hydrogen.

U.S. Pat. No 4,180,689 issued to E. E. Davies et al describes the conversion of $C_3$–$C_8$ aliphatic hydrocarbons to aromatic hydrocarbons in a process which employs a catalyst comprising gallium supported on an aluminosilicate. This reference indicates a temperature between 450 and 700 degrees Celsius, preferably between 500 and 600 degrees Celsius may be employed. U.S Pat. No. 3,761,389 issued to L. D. Rollman et al describes an improved process for converting $C_2$ to 400 degrees Fahrenheit hydrocarbons to aromatics over a ZSM-5 type catalyst. The improvement resides in the use of two reaction stages in series, with the second stage, characterized as an alkylation stage, being held at less severe operating conditions of from 500 to 800 degrees Fahrenheit (260 to 426 degrees Celsius).

U.S. Pat. No. 2,972,643 issued to C. N. Kimberlain, Jr. et al describes the conversion of olefins to higher molecular weight compounds including aromatics over an aluminosilicate-based catalyst at temperatures of 350 to 800 degrees Fahrenheit (177 to 426 degrees Celsius). The catalyst may be exchanged to contain metals. The catalyst is described as a strong adsorbent, and the process is described as including a product recovery operation (column 4, lines 3–13) in which contact with the feed is terminated to allow the recovery of the aromatics.

European patent application No. 85303271.2 naming A. H. P. Hall as the inventor describes a two-step process for the production of liquid products from light aliphatic hydrocarbons. The process of this reference uses a ZSM-5 containing catalyst similar to catalysts which may be used in the subject invention. This reference is also relevant for its teaching in regard to the use of catalyst of different degrees of activity, as regulated by coke deposits on the catalyst, to selectively convert first the olefinic and then the paraffinic feed hydrocarbons. The less active catalyst is used to convert the olefins.

U.S. Pat. No. 4,634,799 issued to E. C. Haun et al. is pertinent for its description of a product recovery method for dehydrocyclodimerization processes. In this method propane and butane are recycled to the reaction zone.

Of the above references it is believed only the Detz et al. and Nevitt et al. references describe the use of hydrogen within the reaction zone. It is also believed that heretofore DHCD processes were directed to conversion of feed hydrocarbons to higher molecular weight hydrocarbons rather than to the simultaneous production of LPG and highpurity aromatics.

BRIEF SUMMARY OF THE INVENTION

The invention is a unique process for the conversion of a feed stream comprising a mixture of $C_3$ and/or $C_4$ paraffins and olefins to two products: (1) high quality LPG rich in $C_3$–$C_4$ paraffins and (2) $C_6$–$C_8$ aromatic hydrocarbons. The essence of the subject process is the ability to in effect selectively convert at least a great majority of the olefinic portion of the feed stream to paraffins or aromatics while retaining most of the paraffinic portion of the feed stream to allow the coproduction of essentially olefin-free LPG. This selective conversion is achieved through the use of low temperature reaction zone operating conditions in the presence of added hydrogen, preferably in combination with a gallium-containing zeolitic catalyst having a low amount of coke deposited on the catalyst. When used for the production of LPG, the invention has the advantage of not requiring the input of hydrogen. Thus the cost of hydrogen is eiiminated.

A broad embodiment of the invention may be characterized as a process which comprises the steps of passing hydrogen and a feed stream comprising at least about 20 mole percent olefinic hydrocarbons having 3 to 4 carbon atoms per molecule and also comprising at least about 30 mole percent paraffinic hydrocarbons having 3 to 4 carbon atoms per molecule into a catalytic reaction zone operated at low severity conditions including a temperature below about 465 degrees Celsius and contacting the feed stream with a solid catalyst comprising gallium, and producing a reaction zone effluent stream comprising $C_6$-$C_8$ aromatics and $C_3$ and/or $C_4$ paraffins, with the reaction zone effluent stream containing less than 10 mole percent olefinic hydrocarbons; and, separating the reaction zone effluent stream by means including fractional distillation into a first product stream, which first product stream is rich in aromatic hydrocarbons and is withdrawn from the process, and a second product stream, which second product stream is rich in paraffinic hydrocarbons having 3 to 4 carbon atoms per molecule and is withdrawn from the process, with the first product stream having a mass flow rate equal to at least 10 wt. percent of the mass flow rate of the feed stream and with the second product stream having a mass flow rate equal to at least 30 wt. percent of the flow rate of the feed stream. The second product stream should contain less than 10 mole % olefins.

BRIEF DESCRIPTION OF THE DRAWING

The drawing is a simplified process flow diagram of a dehydrocyclodimerization process employing the subject invention to convert a feed stream of $C_3$ and $C_4$ olefins and paraffins from line 1 into $C_6$-plus aromatic hydrocarbons removed in line 22, propane of line 26 and butane removed in line 25.

DETAILED DESCRIPTION

Mixtures of light paraffins and olefins result from several widely practiced hydrocarbon conversion practices including fluidized catalytic cracking (FCC) and thermal cracking. When the olefin content of these streams is low or in some cases due to economic conditions it may be most cost effective to hydrogenate the olefins in these mixtures and produce high-quality (low olefin content) LPG. The subject invention provides an alternative to such a hydrogenation requirement by employing a dehydrocyclodimerization zone to convert the feed mixture to LPG and aromatics. The subject invention also eliminates the need to supply hydrogen to hydrogenation zones formerly used to saturate these olefins.

Often olefins are highly desired for use in competing processes such as polymerization and alkylation. In these instances it may be preferable to first consume or extract the olefins and to then feed the remaining paraffin-rich materials to a dehydrocyclodimerization process. However, in other instances the demand for olefins, especially $C_4$ olefins is not as great. For instance, in some geographic locations, especially some Asian locations, there is only a minimal demand for $C_4$ olefins while there is a sizable market for LPG and aromatics. In this situation, it may be preferable to saturate the olefins in a hydrogenation zone to produce high-quality LPG. This would increase the cost of eliminating the olefins. Overall in this situation it would be preferable to selectively convert the olefins to aromatics thereby leaving the light paraffins available for the production of LPG or for other uses.

It is an objective of the subject invention to provide a dehydrocyclodimerization process which is highly selective in producing aromatic hydrocarbons from a mixture of $C_3$ and/or $C_4$ paraffins and olefins while leaving a majority of the paraffins unconverted and available for recovery. It is a further objective of the invention to provide a process which simultaneously hydrogenates feed olefins while performing a limited degree of dehydrocyclodimerization and thereby produces a product substantially lower in olefins than the feed.

The hydrogenation of olefins is not normally considered to be a function of a dehydrocyclodimerization process or reaction. However, it is a primary objective of the subject process. As the process employs a DHCD catalyst in a preferred DHCD reactor configuration and does produce aromatic hydrocarbons by conversion of olefins it will be discussed herein primarily in terms of a DHCD process This is not intended to dismiss the importance of the hydrogenation function of the process. As evidence of this, it can be noted that the subject process can proceed with a net chemical consumption of hydrogen within the reaction zone. This consumption should however be at a rate less than about 50 SCFB (7.4 std $m^3/m^3$).

In the subject process at least 60 and preferably 80 mole percent of any $C_3$ to $C_5$ olefinic hydrocarbons present in the feed stream are converted to either paraffinic or aromatic hydrocarbons. Higher levels of feed olefin conversions may be achieved with suitable recycle arrangements, with such recycling being required primarily due to the tendency for butylene production during propane and/or propylene conversion. Propylene conversion is therefore believed more indicative of olefin conversion rates. Accordingly, propylene conversion (removal) levels greater than 90 mole percent are very highly preferred.

Dehydrocyclodimerization (DHCD) processes for the conversion of light aliphatic hydrocarbons to aromatic or nonaromatic $C_6$-plus hydrocarbons have been the subject of significant development efforts as evidenced by the previously cited references. Heretofore, the basic utility of the process has been considered to be the conversion of available $C_3$ and/or $C_4$ hydrocarbons into the more valuable aromatic hydrocarbons and hydrogen or to convert the feed hydrocarbons to higher molecular weight aliphatic products. This may be desired simply to upgrade the value of the hydrocarbons. It may also be desired to correct an overabundance of the $C_3$ and $C_4$ hydrocarbons or to fulfill a need for the aromatic hydrocarbons. The aromatic hydrocarbons are highly useful in the production of a wide range of petrochemicals, with benzene being one of the most widely used basic feed hydrocarbon chemicals in the production of petrochemicals. The product aromatic hydrocarbons are also useful as blending components in high octane number motor fuels.

The conventional feed compounds to a dehydrocyclodimerization process are light aliphatic hydrocarbons having from 2 to 4 carbon atoms per molecule. Feed streams may comprise a single compound or a mixture of two or more of these compounds including mixtures of olefins and paraffins. The preferred feed compounds for the subject process are propane, propylene, the butanes, and the butylenes, with a mixture of butanes and butylenes being highly preferred. An olefin concentration in the feed above 30 mole % is preferred. However, if the olefin content exceeds about 50 mole percent it will probably be more economically attractive to utilize the olefins via alkylation or oligomerization. Therefore the feed preferably comprises over 50 mole percent paraffinic hydrocarbons. Mixed feed streams preferably contain over 15 mole percent $C_3$ hydrocarbons and over 10 mole percent propylene. A highly preferred feed stream is one containing at least 70 mole percent $C_4$ hydrocarbons. The hydrocarbon feed stream to the process may also contain some $C_2$ and $C_5$ hydrocarbons. It is preferred that the concentration of $C_5$ hydrocarbons in the feed stream to the subject process is held to the minimum practical level. The preferred $C_6$-plus products of DHCD processes are normally $C_6$-$C_8$ aromatic hdyrocarbons. However, dehydrocyclodimerization processes are not 100% selective and small amounts of $C_6$-plus aliphatics and $C_9$-plus aromatics are also produced.

A hydrogen-producing process is normally desired over a hydrogen-consuming process. This is due to the cost of hydrogen. However, if hydrogen is available at the same location as the subject process and/or there is no use for hydrogen discharged from the subject process then it may be desired to operate the process as a hydrogen consuming process. Operating with a net hydrogen consumption is therefore only one alternative embodiment of the subject process. It has been found that control of hydrogen consumption is possible by adjusting the severity of the operating conditions when the preferred catalyst and feed mixtures are utilized. The primary means of increasing the severity of the process is by increasing the average reaction zone temperature. An increase in inlet temperature results in an increase in conversion and the production of more aromatic hydrocarbons. The production of hydrogen via aromatization can thereby be balanced against the consumption of hydrogen via saturation of olefinic feed hydrocarbons. Hydrogen consumption is preferably less than 100 SCFB (14.8 std m3/m3) in the hydrogen consuming mode.

The configuration of the reaction zone and the composition of the catalyst employed within the reaction zone are not basic elements of the invention or limiting characteristics of the invention. Nevertheless, in order to provide a background to the subject invention, it is felt useful to describe the preferred reactor system for use with the invention. This system comprises a moving bed radial flow multi-stage reactor such as is described in U.S. Pat. Nos. 3,652,231; 3,692,496; 3,706,536; 3,785,963; 3,825,116; 3,839,196; 3,839,197; 3,854,887; 3,856,662; 3,918,930; 3,981,824; 4,094,814; 4,110,081; and 4,403,909.

The subject process is preferably limited to practice with a single reaction zone although the reaction zone will normally comprise a number of reaction stages with interheaters. There is therefore no separation or withdrawal of reactants between the stages of the single reaction zone. The above-cited patents also describe catalyst regeneration systems and various aspects of moving catalyst bed operations and equipment. This reactor system has been widely employed commercially for the reforming of naphtha fractions. Its use has also been described for the dehydrogenation of light paraffins.

The preferred moving bed reactor system employs a spherical catalyst having a diameter between about 1/64 and ⅛ inch. The catalyst preferably comprises a support material and a metallic component deposited on the support material as through impregnation or coprecipitation. The previously cited references point out that the current trend is to use a zeolitic support material, with the catalyst referred to in the art as a ZSM-5 type zeolite being often specified as a preferred material. When properly formulated, it appears this zeolitic material by itself has significant activity for the dehydrocyclodimerization reaction. Further information on such zeolitic catalysts for the DHCD reaction can be obtained from European Patent Application No. 83 201 1422.9 by E. P. Kieffer. However, it is still preferred to employ a metallic component within the catalyst system to increase the aromatic selectivity of the catalyst. The preferred metallic component is gallium as described in the previously cited U.S. Pat. No. 4,180,689. The catalyst may contain from about 0.15 to 2.4 weight percent gallimm which is preferably exchanged or impregnated into the zeolitic component of the catalyst rather than forming a portion of the original (as produced) zeolite. A preferred range of the gallium component is from 0.3 to 1.0 weight percent. A suitable catalyst is described in U.S. Pat. No. 4,636,483 issued to S. S. Kjell et al. which is incorporated herein by reference.

The zeolitic material, preferably ZSM-5, is normally bound with another material during the particle forming stage to increase the strength and durability of the catalyst. This binding material is often a form of clay or alumina. It is highly preferred that this binder comprises a phosphorous-containing alumina, as can be prepared by the gelation of a hydrosol precursor in accordance with the well-known oil-dropping method. For instance, $H_3PO_4$ may be admixed with an alumina hydrosol prepared by digesting aluminum in aqueous hydrochloric acid and/or aluminum chloride solution. The finished catalyst should have a phosphorous to aluminum ratio of from about 1:1 to about 1:100. The aluminosilicate or zeolite can be admixed into the phosphorous-containing alumina. The final composite can be formed in a variety of shapes using standard methods or by oil-dropping and then finished using conventional catalyst manufacturing techniques.

In the subject process, the dehydrocyclodimerization reaction zone is preferably operated at a temperature between about 734°–907° Fahrenheit (390°–485° Celsius) and a pressure under 125 psig (861 kPa g). A temperature under 465 degrees C. is preferred and a temperature below about 425 degrees C. is highly preferred in order to provide the desired "mild" dehydrocyclodimerization conditions. The DHCD reaction is normally favored by lower pressures, and pressures under about 70 psig (483 kPa g) at the oullet of the reaction zone are highly preferred. The liquid hourly space velocity should be between 0.4 and 5.0 hr$^{-1}$. The reaction conditions should include hydrogen in sufficient quantity to maintain a hydrogen to feed $C_3$-plus hydrocarbon mole ratio of from 0.3 to 2.8. The addition of makeup hydrogen feed gas may be necessary. It is preferred to recycle hydrogen-rich gas recovered from the reactor effluent.

The drawing illustrates a preferred embodiment of the invention. Those skilled in the art will recognize that this process flow diagram has been simplified by the elimination of many necessary pieces of process equipment including some heat exchangers, process control systems, pumps, fractionation column overhead and reboiler systems, etc. normally employed on a process such as this but which are not necessary to an understanding of the process. It may also be readily discerned that the process flow presented in the drawing may be modified in many aspects without departing from the basic overall concept of the invention. For example, the heat exchangers shown in the drawing have been held to a minimum for purposes of simplicity. In a process as complex as this, there exists many possibilities for indirect heat exchange between different process streams.

Referring now to the drawing, a feedstream comprising a mixture of propane, propylene, butanes and butylenes is fed to the process through line 1. This feedstream is combined with a hydrogen-rich recycle gas stream from line 2 and is passed through line 3 into the dehydrocyclodimerization reaction zone 4. In addition to a reactor, this zone preferably contains a feed-effluent indirect heat exchange means and heating means as required to vaporize and heat the entering feed materials to the desired inlet temperature for the reactor(s). The preferred form of the reactor is the multi-stage radial flow moving bed system having interstage heating as described herein. The feed stream of line 1 may be either a liquid phase stream or alternatively a vapor phase stream which has already been heated to the desired reaction conditions. In the latter case, it may not be necessary to provid heaters and indirect heat exchange within the overall dehydrocyclodimerization reaction zone. Within the reaction zone, the recycled gases and feed stream are contacted with the solid catalyst under the mild conditions set out herein. This effects the conversion of propylene and butylenes into aromatic hydrocarbons, propane and butane and the production of a dehydrocyclodimerization reaction zone effluent stream which comprises an admixture of hydrogen, unreacted feed hydrocarbons and product aromatic hydrocarbons which will predominate in benzene, toluene and $C_8$ aromatics including xylenes and a minor amount of light by-products such as methane and ethane.

The effluent of the dehydrocyclodimerization reaction zone is passed through line 5 and is subjected to sufficient cooling in an indirect heat exchange means 6 to effect the condensation of substantially all of the $C_6+$ hydrocarbons contained therein and also to effect the condensation of at least some $C_3$ and $C_4$ hydrocarbons. The thus partially condensed effluent stream is passed into a first vapor-liquid separation vessel 7 wherein the entering materials are separated into a liquid phase hydrocarbon stream withdrawn through line 17 and a vapor phase stream withdrawn through lin 8. The liquid phase stream of line 17 comprises the $C_6$ product aromatic hydrocarbons admixed with $C_3$ and $C_4$ hydrocarbons.

The vapor stream removed from the separator through line 8 comprises hydrogen, uncondensed $C_3$ and $C_4$ hydrocarbons, and the majority of the by-product light hydrocarbons including ethane produced in the process. A portion of this gas is vented from the process through line 10 as a fuel gas or other net off-gas stream. The purpose of this stream is the discharge of the small amount of light by-products including ethane and methane which are produced in the process. The remaining portion of the vapor phase stream is passed through line 9 and compressed in the compressing means 11. This vapor stream is then transported via line 12 through the indirect heat exchange means 13 and into a second vapor-liquid separation zone 14. The heat exchange means 13 is another cooler employed to effect a further partial condensation of the material flowing through line 12. This effects a further condensation ff the propane and butanes which are present in the material of line 12. The material entering the second vapor-liquid separation zone is separated therein into a liquid phase stream, which is rich in $C_3$-$C_4$ hydrocarbons and is withdrawn through line 18, and a vapor phase recycle stream comprising hydrogen and a minor amount of light hydrocarbons which is withdrawn in line 15. The recycle gas stream is passed through lines 15 and 28 and if necessary admixed with a make-up hydrogen stream from line 16 to counteract any net hydrogen consumption which occurs within the dehydrocyclodimerization reaciion zone. The resultant hydrogen-rich gas stream is then passed through lines 2 and 3 to the reaction zone. In this mode of DHCD operation it is not believed necessary to recycle ethane. Some ethane will however be present in the recycle gas.

The liquid phase material of line 18 is combined with the liquid from line 17 and passed through line 19 into a debutanizer column 20. The unreacted feed and product $C_3$-$C_4$ hydrocarbons and any lighter hydrocarbons dissolved in the entering liquid are removed as a net overhead stream carried by line 21, while the product aromatic hydrocarbons are withdrawn from the process as the net bottoms product of the column through line 22. The net bottoms stream becomes the first product stream of the subject invention. The overhead condensing system which would typically be employed to effect refluxing of the debutanizer column and the reboiling means employed in the operation of this column are not shown. The net overhead stream of the debutanizer may be withdrawn from the process via line 23 as a second product stream.

In an alternative flow the net overhead stream of the debutanizer column is passed via line 21 into a splitting column 24. A net bottoms stream removed from this fractional distillation column is rich in butanes and is withdrawn from the process in line 25. The net overhead stream of the splitting column may also be removed as a net product stream, which is rich in propane. Depending on the concentration of propylene in the overhead stream of line 26, it may be desired or necessary to recycle some of this material to the DHCD reaction zone via line 27 in order to reduce the olefin content of this stream. This may be necessary to meet standards for the maximum acceptable amounts of olefins in the propane stream. A portion of the butane-rich bottoms stream of column 24 or a portion of the overhead stream of fractionation column 20 may also be recycled by optional lines 29 and 23 if desired.

A preferred embodiment of the invention may accordingly be characterized as a dehydrocyclodimerization process which comprises the steps of passing hydrogen and a feed stream comprising at least 30 mole percent olefins having 3 to 4 carbon atoms per molecule and also comprising at least 50 mole percent paraffins having 3 to 4 carbon atoms per molecule and containing less than 10 mole percent $C_5$-plus hydrocarbons into a catalytic reation zone and contacting the feed stream with a solid catalyst comprising a zeolite and gallium at low severity conditions including an inlet temperature below 450 degrees Celsius, which conditions result in the total amount of carbon which is deposited on the catalyst after 100 hours of onstream operation being less than about 8 weight percent, and producing a reaction zone effluent stream comprising $C_6$-$C_8$ aromatic hydrocarbons and $C_3$-$C_4$ paraffins; and, separating the reaction zone effluent stream by fractional distillation into at least a first product stream rich in aromatic hydrocarbons and a second product stream rich in paraffinic hydrocarbons, with the flow rate of the second product stream being greater than the mass flow rate of said paraffinic hydrocarbons in said feed stream.

It is believed that those skilled in the art of petroleum and petrochemical process design myy determine proper operating conditions, fractionation column and separation vessel designs, and operating procedures for the equipment used in the subject process through the use of standard process design techniques after having now been appraised of the overall flow of the process.

The vapor-liquid separation zones employed within the process preferably comprise a suitably sized vertically oriented vessel having a demisting pad or other liquid entrainment removal means provided at the upper end. The fractionation zone employed in the process preferably contains one or more trayed fractionation column(s) having sieve-type trays and being of relatively standard design. For instance, the product recovery column may contain 30 trays. The operating conditions required in the fractionation zone are dependent upon the hydrocarbons being separated and the desired separation, but suitable fractionation columns may be readily designed by those skilled in the art.

EXAMPLE 1

A pilot plant study was performed to evaluate the performance of the subject process in handling a simulated $C_3$ fluidized catalytic cracking (FCC) stream produced by blending pure components to yield a feed stream comprising 65 weight percent propylene and 35 weight percent propane. This composition is representative of what would be produced by a modern high severity FCC unit. The feed stream was processed at a temperature of 415 degrees Celsius, a liquid hourly space velocity of 1.0 hr.$^{-1}$, a pressure of 75 psig (517 k Pa g) and a hydrogen to hydrocarbon molar ratio of 0.50 at the reactor inlet. The catalyst was produced following the preferences set out herein and contained about 0.7 weight percent gallium and about 67 percent zeolite in a bound oil-dropped sphere. After 50 hours of onstream operation, the conversion of propylene was 99.6 mole percent and the product distribution was as given in the following table. The majority of the aromatics formed were benzene, toluene and xylenes. After 100 hours of onstream operation, the carbon content of the catalyst was 6.8 weight percent.

TABLE

| Selectivities, wt. %, for Example 1 | |
| --- | --- |
| Hydrogen | −0.5 |
| $C_1/C_2$ | 13.6 |
| $C_3H_8$ | 25.3 |
| $C_4H_{10}$ | 12.3 |
| $C_4H_8$ | 9.9 |
| $C_5H_{12}$ | 2.7 |
| $C_6H_{14}$ | 0.3 |
| Aromatics | 36.4 |

The above data indicates the effluent was essentially free of propylene. The olefins present were butylenes. The butylenes are believed to be reaction intermediates between propane or propylene and aromatic hydrocarbons which are produced near the exit from the reaction zone and hence were swept from the catalyst prior to the completion of the later steps in the reaction sequence. The process therefore is capable of converting $C_3$ hydrocarbons into $C_4$ saturated and unsaturated hydrocarbons. The $C_4$ hydrocarbons can be readily separated by fractionation from the $C_3$ hydrocarbons to yield separate $C_3$ and $C_4$ product streams in addition to an aromatic hydrocarbon-rich product stream. A portion of the $C_4$ fraction may be recycled to reduce the ultimate butylene concentration of the $C_4$ fraction. The $C_5$ hydrocarbons may be left in the aromatic fraction, especially if the aromatics are use as a gasoline blending component.

EXAMPLE 2

The procedure of Example 1 was repeated except no hydrogen was added to the feed stream. Propylene conversion was again almost 100 percent while aromatics selectivity increased to 45 weight percent. The carbon content of the catalyst after 100 hours of operation increased to about 13 weight percent indicating a lower reaction temperature or more frequent regeneration would be required.

The selectivity of olefin conversion to aromatic hydrocarbons is dependent upon catalyst activity and the length of time the catalyst has been previously used. The effects of these factors can be correlated, or perhaps more correctly, are related to the amount of carbonaceous deposits, often referred to as coke, present on the catalyst particles. It has been observed that as the amount of coke or carbon deposited on the catalyst particles increases, the selectivity to aromatics production decreases. It is therefore desirable to operate the process having the lowest practical carbon level on the catalyst. The preferred continuous catalyst regeneration system and moving bed reactor provide a means for maintaining a low carbon level on the catalyst without interrupting the operation of the process for shutdown and carbon burnoff procedures.

With a fixed multibed reactor system, the amount of carbon on the catalyst should be fairly uniform within each bed of catalyst although it could vary between catalyst beds depending on reaction conditions. With the preferred moving bed system, the highest carbon level will be found on the catalyst which is being withdrawn from the bottom of the reactor, and the catalyst entering the top of the reactor will have a very low carbon level. In a moving bed system, the carbon level is therefore measured on the exiting catalyst. In a fixed bed system, the level of carbon deposition can be determined through the use of various types of known catalyst sampling apparatus. The reaction zone should be operated under low severity conditions which result in the total amount of carbon deposited upon the catalyst particles after the equivalent of 100 hours of continuous operation of the process being less than about 8 weight percent. This 100 hour time period is chosen for use in this criterion as it corresponds to the average 4-day catalyst residence cycle or onstream time envisioned for operation of the reaction zone. The average carbon level on the total amount of catalyst in the moving bed reactor will be about one-half of this or 4 weight percent. Preferably the amount of carbon on the catalyst after 100 hours of continuous usage is less than about 7 weight percent with the average catalyst carbon level being less than 3.5 weight percent.

It is readily apparent that processes operating with only short catalyst usage times between regenerations will probably not accumulate as much carbon. The subject criteria is therefore based upon the amount of carbon deposition which would occur if the catalyst is actually used for 100 hours without intermediate regeneration, but the total amount of carbon on the catalyst is still subject to the same basic limitations irrespective of the actual prior usage of the catalyst. Therefore, the catalyst should not be allowed to accumulate 8 weight percent carbon in a fixed bed operation, and preferably contains less than 7 weight percent carbon independent of the length of time it has been used.

It is preferred that the hydrocarbons recovered from the effluent of the reaction zone do not contain appreciable amounts of $C_6$-plus non-aromatic hydrocarbons. This is due to the increased value of high-purity aromatics and the difficult and expensive separation steps required to remove co-boiling non-aromatics from aromatics. The liquid-phase stream resulting from partial condensation of the reaction zone effluent stream and withdrawn from the vapor-liquid separation zone may be separated by simple fractionation into a $C_6$-plus fraction having a very high (above 95 weight percent) aromatics content and a $C_3$-$C_5$ fraction which has an olefin content which is less than onehalf that of the feed stream. Preferably the $C_3$-$C_5$ fraction has an olefin molar concentration less hhan 40 percent of that of a $C_3$-$C_5$ feed stream. The paraffin-rich product stream(s) of the subject process should accordingly contain less than 10 mole percent total $C_3$-$C_5$ olefins and preferably less than 2 mole percent olefins. The $C_6$-plus fraction can then be further separated by fractional distillation to provide product streams rich in benzene, toluene, and $C_8$ aromatics if so desired. As used herein the term "rich" is intended to indicate a molar concentration of the indicated compound or class of compounds greater than 75 percent.

Another embodiment of the invention is a hydrocarbon conversion process for the production of aromatic hydrocarbons and LPG from a mixture of $C_3$-$C_4$ olefins and paraffins in which a hydrocarbon feed stream comprising at least 30 mole percent butanes and at least 30 mole percent butylenes is passed into a single catalytic reaction zone operated at dehydrocyclodimerization conditions and contacted with a solid catalyst comprising gallium, and a reaction zone effluent stream comprising $C_6$-$C_8$ aromatic hydrocarbons and butanes is produced; the reaction zone effluent stream is separated by fractionation and a first product stream is produced, which first product stream is rich in $C_6$-$C_8$ aromatic hydrocarbons and is withdrawn from the process, characterized in that the reaction zone is operated at low severity dehydrocyclodimerization conditions which include a temperature below 450 degrees Celsius, and in that a second product stream which is rich in butanes is also produced by fractionation and is withdrawn from the process, with the second product stream having a flow rate equal to at least 30 wt. percent of the mass flow rate of the feed stream such that there is a net production of paraffinic hydrocarbons within the reaction zone. hhe mass flow rate of the second (paraffinic) product stream is preferably equal to at least 50 wt. percent of the flow rate of the feed stream.

What is claimed:

1. A hydrocarbon conversion process which comprises passing a hydrocarbon feed stream comprising at least 30 mole percent olefins having 3 to 4 carbon atoms per molecule and also comprising at least 50 mole percent paraffins having 3 to 4 carbon atoms per molecule and containing less than 10 mole percent $C_5$-plus hydrocarbons into a catalytic reaction zone operated at low severity conditions and contacting the feed stream with a solid catalyst comprising gallium, and producing a reaction zone effluent stream comprising $C_6$-$C_8$ aromatic hydrocarbons and $C_3$-$C_4$ paraffins, with the reaction zone effluent stream containing less than 10 mole percent olefinic hydrocarbons; with said low severity conditions including a combination of pressure, feed space velocity and temperature, including a temperature below 425° C., which result in a partial conversion of the feed hydrocarbons into aromatic hydrocarbons and whereby (i) when the effluent is separated there are produced a first product stream, which first product stream is rich in $C_6$-$C_8$ aromatic hydrocarbons and is withdrawn from the process, and a second product stream, which second product stream is rich in $C_3$-$C_4$ paraffins and is withdrawn from the process, with the second product stream having a flow rate equal to at least 30 wt. percent of the flow rate of the feed stream; and (ii) the mass flow rate of paraffinic hydrocarbons out of the reaction zone exceeds the mass flow rate of paraffinic hydrocarbons into the reaction zone.

2. The process of claim 1 further characterized in that the reaction zone is operated under conditions which result in the total amount of carbon deposited upon the catalyst after 100 hours of continuous operation being less than 7 weight percent.

3. The process of claim 2 further characterized in that the catalyst also comprises phosphorous and has a phosphorous to aluminum ratio of about 1:1 to about 1:100.

4. The process of claim 1 further characterized in that the process is performed with a net consumption of hydrogen occurring within the reaction zone.

5. The process of claim 1 further characterized in that the paraffinic hydrocarbon of the second product stream is butane, and in that a process stream rich in $C_3$ hydrocarbons is also recovered from the reaction zone effluent stream by fractional distillation.

6. The process of claim 5 further comprising recycling a first aliquot portion of the process stream to the reaction zone and withdrawing a second aliquot portion as a third product stream.

7. The process of claim 1 further characterized in that the second product stream contains less than 2.0 mole percent olefinic hydrocarbons.

* * * * *